(12) United States Patent
Haik

(10) Patent No.: US 8,951,501 B2
(45) Date of Patent: Feb. 10, 2015

(54) NONINVASIVE THERMOMETRY MONITORING SYSTEM

(75) Inventor: Yousef Haik, Greensboro, NC (US)

(73) Assignees: University of North Carolina at Greensboro, Greensboro, NC (US); United Arab Emirates University, Al Anin (AE)

( * ) Notice: Subject to any disclaimer, the term of this patent is extended or adjusted under 35 U.S.C. 154(b) by 0 days.

(21) Appl. No.: 13/430,274

(22) Filed: Mar. 26, 2012

(65) Prior Publication Data
US 2012/0184872 A1 Jul. 19, 2012

Related U.S. Application Data

(62) Division of application No. 12/205,565, filed on Sep. 5, 2008.

(60) Provisional application No. 60/970,566, filed on Sep. 7, 2007, provisional application No. 60/971,286, filed on Sep. 11, 2007, provisional application No. 61/027,449, filed on Feb. 9, 2008.

(51) Int. Cl.
| | |
|---|---|
| *A61K 33/24* | (2006.01) |
| *A61K 41/00* | (2006.01) |
| *A61K 47/48* | (2006.01) |
| *A61K 49/18* | (2006.01) |
| *B82Y 5/00* | (2011.01) |

(52) U.S. Cl.
CPC ....... *A61K 47/48853* (2013.01); *A61K 41/0052* (2013.01); *A61K 49/1851* (2013.01); *B82Y 5/00* (2013.01)

USPC ....... 424/9.3; 424/9.321; 424/9.323; 424/9.1; 424/9.6

(58) Field of Classification Search
USPC ........... 424/9.321, 9.323, 1.11, 9.1, 9.32, 9.6, 424/617, 641, 646; 435/325
See application file for complete search history.

(56) References Cited

U.S. PATENT DOCUMENTS

| | | | |
|---|---|---|---|
| 5,916,539 A | 6/1999 | Pilgrimm | |
| 6,514,418 B1 | 2/2003 | Bartscherer et al. | |
| 7,427,393 B2 * | 9/2008 | Takeyama | 424/9.321 |
| 2004/0234455 A1 * | 11/2004 | Szalay | 424/9.6 |
| 2005/0249817 A1 * | 11/2005 | Haik et al. | 424/617 |
| 2010/0285135 A1 * | 11/2010 | Wendorf et al. | 424/489 |
| 2011/0256621 A1 * | 10/2011 | Albrecht et al. | 435/325 |

* cited by examiner

*Primary Examiner* — Michael G Hartley
*Assistant Examiner* — Jagadishwar Samala
(74) *Attorney, Agent, or Firm* — Akerman LLP; Michael K. Dixon

(57) ABSTRACT

A noninvasive thermometry monitoring system for determining a temperature of tissue to which hyperthermia treatment is administered is disclosed. The monitoring system may incorporate magnetic nanoparticles having known moments such that once exposed to an alternating magnetic field, the magnetic nanoparticles increase in temperature. Imaging systems can disclose the magnetic nanoparticles within a patient. The temperature of the magnetic nanoparticles can be determined by comparing the magnetic nanoparticle with known temperatures for that type of magnetic nanoparticle. The image of the magnetic nanoparticles may be compared with surrounding tissue to determine the temperature of the surrounding tissue that is exposed to hyperthermia treatment.

5 Claims, 5 Drawing Sheets

NONINVASIVE THERMOMETRY MONITORING SYSTEM

CROSS-REFERENCE TO RELATED APPLICATION

This application is a divisional application of U.S. patent application Ser. No. 12/205,565, filed Sep. 5, 2008, which claims the benefit of U.S. Provisional Patent Application No. 60/970,566, filed Sep. 7, 2007, U.S. Provisional Patent Application No. 60/971,286, filed Sep. 11, 2007 and claims the benefit of U.S. Provisional Patent Application No. 61/027,449, filed Feb. 9, 2008, all of which are incorporated by reference.

FIELD OF THE INVENTION

This invention is directed to a patient monitoring systems, and more particularly, to a noninvasive thermometry monitoring system configured to monitor the hyperthermia treatment systems.

BACKGROUND OF THE INVENTION

Procedures such as hyperthermia, treatment of cardiac arrhythmias and heat sensitive promoters in gene therapy require temperature change monitoring. Magnetic resonance imaging (MRI) thermometry overcomes problems associated with invasive temperature monitoring techniques such as thermocouples and fiber optics. In the current MRI thermometry the temperature variation is detected by measuring small changes in the proton resonant frequency, longitudinal relaxation time or apparent diffusion coefficient. However, these techniques have low temperature sensitivity and are influenced by the local motion and magnetic susceptibility variation. Liposome-encapsulated gadolinium chelates that have phase change characteristics have been used to monitor temperature. In particular, the temperature during the phase transition can be indicative of the local tissue temperature. However, this technique provides only a single value for the temperature, not a map of temperature distribution Furthermore, this technique requires careful design for the carrier and thus can be unreliable.

Heating organs and tissues as a treatment of cancer is well known. The first reference to link heat and the destruction of cancerous growths was as early as 3000 BC in the contents of an Egyptian papyrus and later in the writings of Hippocrates. More scientifically, the connection between disappearance of tumors and high fever, either from infections or artificially induced by bacterial toxins, have initiated a concept of thermotherapy. Reports on enhanced selective thermal sensitivity of animal tumors compared with normal tissue confirm that hyperthermia may be considered as a cytotoxic agent. There has been work conducted on all aspects of heat application to tumors, which lead to rapid development in therapeutic applicator design and to sophistication of hyperthermia equipment.

Hyperthermic temperatures increase blood circulation in tumors. The increase in temperature increases the presence of oxygen-bearing blood in tumor tissues, which is critical for increasing the effectiveness of ionizing radiation. Ionizing radiation, also referred to as radiotherapy, destroys tumor cells substantially through the formation of oxygen radicals that attack cell DNA of a tumor. Oxygen-starved cells are three-times more resistant to ionizing radiation than are normal cells. Low oxygen levels in human tumors, referred to as hypoxia, have been linked to failure in achieving local tumor control through ionizing radiation. In addition, the degree of oxygen deficiency in cancerous tumors is a key predictor of the efficacy of ionizing radiation therapy. Results from molecular biology research demonstrate that hyperthermia treatments may be used in many different tumors particularly for local tumor control. Such hyperthermia treatments resulted in an increase in the survival rate of the patients, especially when hyperthermia was combined with radiation therapy.

MRI has been used to facilitate a noninvasive technique to monitor tissue conditions. Tissue temperature change in a patient have been identified using many parameters in MRI, such as, proton density, T1 relaxation time, T2 relaxation time, diffusion coefficient, magnetization transfer and proton resonant frequency shift. These techniques, however, suffer from various limitations, such as lack of linearity, low sensitivity, dependence on tissue type, sensitivity to motion, sensitivity to susceptibility artifacts, relative temperature measurement and interrelationship with many MRI parameters.

SUMMARY OF THE INVENTION

This invention is directed to a noninvasive thermometry monitoring system for determining a temperature of tissue within a patient, such as a human or animal. The noninvasive thermometry monitoring system may be used to determine the temperature of tissue to which hyperthermia treatment is administered or inflammation mediated temperature variation at tissues. The noninvasive thermometry monitoring system may include at least one monitoring agent, which may be a magnetic nanoparticle, having a known magnetic moment profile that correlates with particular temperatures. As such, the magnetic nanoparticle may be administered to a patient undergoing hyperthermia treatment to noninvasively determine the temperature of the target tissue. In hyperthermia treatment, the noninvasive thermometry monitoring system may be used to determine whether the target tissue is being heated as desired and to what temperature the target tissue is being heated.

Material with a detectable physical property at different temperatures provides a suitable alternative for thermo-mapping at different locations. Coupling the temperature dependence with a physical quantity that can be detected noninvasively provides a unique technique for temperature mapping in deep-seated tissue. Magnetic nanoparticles that have magnetic moment temperature dependence can provide the desired multifunctional actions. Magnetic nanoparticles have a contrast ability signature, temperature signature, and can be utilized as agents for hyperthermia therapy. The difference in magnetic moment between magnetic nanoparticles and surrounding tissue creates a contrast in the magnetic resonance imaging. Magnetic nanoparticles with steep variation in their magnetic moment as a function of temperature elevation provide information about the tissue temperature.

This invention is related to a noninvasive thermometry monitoring system that employs novel thermometry agent. The monitoring agent may be formed from one or more magnetic nanoparticles having a Curie temperature less than a critical temperature of tissue at which the tissue is compromised. The Curie temperature of the magnetic nanoparticle may be less than 44° C., such as between about 40° C. and about 44° C. The monitoring agent may be coated with a biocompatible, thermosensitive coating.

The noninvasive thermometry monitoring system may include a magnetic field generator and at least one magnetic nanoparticle having a known magnetic moment profile. The at least one magnetic nanoparticle may also include a biocompatible, thermosensitive coating encapsulating the at least one magnetic nanoparticle. The magnetic nanoparticle may be formed from materials, such as, but not limited to ZnGdFeO. The magnetic nanoparticle may be formed from a combination of magnetic and nonmagnetic materials. The magnetic nanoparticle may have a cross-sectional width of between five nm and one micron.

The encapsulated monitoring agent may be attached to an attenuated bacteria strain. In particular, the encapsulated monitoring agent may be uploaded to an attenuated bacteria strain. The bacteria strain with the encapsulated monitoring agent may readily enter and reside in a tumor within a living being, such as a human or animal, when placed into a bloodstream of the living being. Utilizing attenuated bacteria as a carrier overcomes the issues associated with tagging and delivering conventional monitoring agents to a site of interest such as a tumor. Genetically modified strains of bacteria, such as, but not limited to, *Salmonella typhimurium*, have been shown to accumulate at tumor sites when injected in tumor-bearing mice and clear rapidly from blood in normal mice. The innovative delivery system makes use of genetically modified strains of bacteria, which includes genetically stable attenuated virulence (deletion of purl gene), reduction of septic shock potential (deletion of msbB gene) and antibiotic susceptibility.

The monitoring agents may be delivered to tumors within a patient with a delivery system in which the at least one magnetic nanoparticle is encapsulated with a biocompatible coating and is attached to an attenuated bacteria strain. In particular, the magnetic nanoparticles may be uploaded to attenuated bacteria strains. The predetermined concentration of bacteria may be placed, through injection or otherwise, into a bloodstream of a patient, such as a human being or animal, to identify tumors within the patient. Once in the bloodstream, the bacteria seeks the tumor. Once the bacteria locates the tumor, the bacteria enters the tumor and resides therein. If no tumor is present, the attenuated bacteria strains are passed out of the patient within 24 hours of being injected into the patient.

An alternating magnetic field may then be applied in proximity of the tumor location 24 hours after administering the loaded bacteria to the patient. The alternating magnetic field induce heating within the magnetic nanoparticles. A scan may be performed to develop an image of the magnetic nanoparticles and the surrounding tissue. The image of the magnetic nanoparticles is then compared with the surrounding tissue in the image to determine the temperature of the surrounding tissue.

An advantage of this invention is that the monitoring system enables the temperature of tissue subjected to hyperthermia treatment to be identified to increase the effectiveness of the hyperthermia treatment.

Another advantage with this invention is that the monitoring agents may be attached to bacteria strains that are readily taken up by tumors, thereby effectively delivering the monitoring agents to tumors such that the tumors may be easily be scanned to determine the temperature of the tumors.

These and other embodiments are described in more detail below.

BRIEF DESCRIPTION OF THE DRAWINGS

The accompanying drawings, which are incorporated in and form a part of the specification, illustrate embodiments of the presently disclosed invention and, together with the description, disclose the principles of the invention.

DETAILED DESCRIPTION OF THE INVENTION

Figure 1:
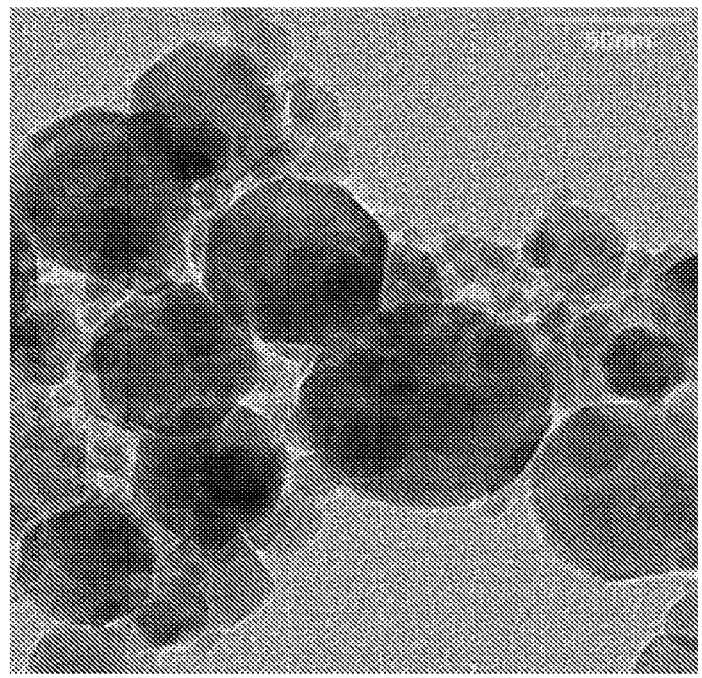
FIG. 1 is a transmission electron microscopy image of a thermosensitive polymer encapsulating a biocompatible self-controlled magnetic nanoparticle.

As shown in FIGS. 1-11, the invention is directed to a noninvasive thermometry monitoring system for determining a temperature of tissue to which hyperthermia treatment is administered. The noninvasive thermometry monitoring system may include at least one monitoring agent, which may be a magnetic nanoparticle, having a magnetic moment profile that correlates with particular temperatures. As such, the magnetic nanoparticle may be administered to a patient undergoing hyperthermia treatment to noninvasively determine the temperature of the target tissue. Therefore, the noninvasive thermometry monitoring system may be used to determine whether the target tissue is being heated as desired and to what temperature the target tissue is being heated.

Hyperthermia treatment may be administered in any known manner or an any manner yet to be invented. The noninvasive thermometry monitoring system may be employed to determine the temperature of the target tissue within a patient. No longer must the temperature of the target tissue be left to guesswork. Rather, the noninvasive thermometry monitoring system may determine the temperature of the target tissue.

The magnetic nanoparticles may be formed from particles having cross-sections between five nm to less than one micron in width. In other embodiment, the magnetic nanoparticles may be larger particles. As used herein, the term "magnetic nanoparticles" includes magnetic, paramagnetic, superparamagnetic ferromagnetic and ferrimagnetic materials. The nanoparticles may be formed from a combination of magnetic and nonmagnetic materials. Such combinations may be configured to have a Curie temperature between about 40° C. and about 44° C. As such, when the magnetic nanoparticles are excited by an alternating magnetic field, the magnetic nanoparticles experience a temperature rise up to but not exceeding their Curie temperature. The magnetic nanoparticles may be synthesized using chemical or physical methods. The magnetic nanoparticles may include CuNi (binary nanoparticle), MnGdFe, ZnGdFe (tri nanoparticle), ZnGdFeO, MnZnGdFe (quad nanoparticle) and other appropriate materials.

For instance, the magnetic nanoparticles may be formed using co-precipitation method and borohydride reduction method. For example, FeGdB and FeNdB nanoparticles have been synthesized using a borohydride reduction method. Ultrasonication was used to form homogeneously sized particles in the nanometer range (30-100 nm). In order to minimize the oxidation effect, these particles were passivated overnight under a continuous flow of oxygen and nitrogen. These particles were further coated with silica by using a precipitation process and have been designed for biomedical applications. Silica coated particles are capable of chemically attaching to proteins and many other biological molecules. Morphology and sizes of all of the magnetic nanoparticles were determined with scanning transmission electron microscopy (TEM).

In an example, the noninvasive thermometry system was studied using six concentrations of MnGdFe nanoparticles ranging from 0 mmol/kg to 0.3 mmol/kg that were impeded in cellulose solution to model tissue structure. The solutions were heated to temperatures below and above the particles' Curie temperature, which was 42.8 degrees Celsius. The suspensions were imaged in a 1.5 tesla human MRI machine. R2 values, which are equivalent to 1/T2 and are measured (in units $ms^{-1}$) for the different concentrations at different temperatures, are shown in Table 1.

TABLE 1

R2 Values at different concentrations and temperatures

| C | Temp (° C.) | | | |
|---|---|---|---|---|
| (mmol/kg) | 20 | 40 | 50 | 60 |
| C 0.0 | 0.0116 | 0.0128 | 0.0119 | 0.0099 |
| C 0.025 | 0.0200 | 0.0224 | 0.0196 | 0.0166 |
| C 0.05 | 0.0252 | 0.0279 | 0.0253 | 0.0216 |
| C 0.1 | 0.0418 | 0.0479 | 0.0465 | 0.0436 |
| C 0.2 | 0.0630 | 0.0733 | 0.0715 | 0.0695 |
| C 0.3 | 0.0842 | 0.0967 | 0.0962 | 0.0982 |

The values in Table 1 were extracted from the full experimental data as shown in FIGS. 4-11. Spin-echo signal (a.u.), which are shown in FIGS. 4-7, is plotted versus the echo-time (ms). A single exponential curve was fitted to the data using non-linear programming (Levenberg-Marquardt) minimizing an error function. Relaxation rate constants (R2) were also plotted, as shown in FIGS. 8-11, as a function of concentration and showed the expected linear dependence for this range of concentration. The relaxivity ($\alpha_2$) values are summarized in Table 2 below. The following equation was used to fit relaxation data as function of concentration $R_2=R_{2i}+a_{\square}C$, where $R_2$ is the observed transverse relaxation rate at concentration C, $R_{2i}$ is the relaxation rate of the control sample and $a_2$ is obtained as the slope of the linear fitted data.

TABLE 2

$\alpha_2$ values at different temperatures

| Temp (° C.) | $\alpha_2$ |
|---|---|
| 20.0 | 0.2403 |
| 40.0 | 0.2799 |
| 50.0 | 0.2839 |
| 60.0 | 0.2982 |

In at least one embodiment, the magnetic nanoparticles may be encapsulated by one or more biocompatible coatings. The encapsulated monitoring agents may have a cross-section between about 10 nm and one micron. The biocompatible coating may be, but is not limited to, a polymeric material, a biodegradable material, and a protein. A polymeric material may be, but is not limited to, one or more oligomers, polymers, copolymers, or blends thereof. Examples of polymers include polyvinyl alcohol; polyethylene glycol; ethyl cellulose; polyolefins; polyesters; nonpeptide polyamines; polyamides; polycarbonates; polyalkenes; polyvinyl ethers; polyglycolides; cellulose ethers; polyvinyl halides; polyhydroxyalkanoates; polyanhydrides; polystyrenes; polyacrylates, polymethacrylates; polyurethanes; polypropylene; polybutylene terephthalate; polyethylene terephthalate; nylon 6; nylon 6,6; nylon 4,6; nylon 12; phenolic resins; urea resins; epoxy resins; silicone polymers; polycarbonates; polyethylene vinylacetate; polyethylene ethyl acrylate; polylactic acid; polysaccharides; polytetrafluoroethylene; polysulfones and copolymers and blends thereof. The polymeric material may be biocompatible and may be biodegradable. Examples of suitable polymers include ethylcelluloses, polystyrenes, poly(ε-caprolactone), poly(d,l-lactic acid), polysaccharides, and poly(d,l-lactic acid-co-glycolic acid). The polymer may be a copolymer of lactic acid and glycolic acid (e.g., PLGA). The protein may be, but is not limited to, BSA or HSA.

In one embodiment, the monitoring agents may be uploaded to attenuated bacteria strains to facilitate greater uptake by a tumor of the monitoring agents. The attenuated bacteria strains may be genetically modified strains of bacteria, including genetically stable attenuated virulence (deletion of purI gene), reduction of septic shock potential (deletion of msbB gene) and antibiotic susceptibility. In one embodiment, the attenuated bacteria strain may be, but is not limited to, *Salmonella*. The monitoring agents that are uploaded to the attenuated bacteria strains may be encapsulated by the biocompatible coating.

The monitoring agents may be uploaded to attenuated bacteria strains via incubating the bacteria with the monitoring agents. For example, experiments were conducted in which magnetic nanoparticles ranging from 80-120 nm in size were utilized. As can be seen from Table 3, the conditions of incubating the bacteria with magnetic nanoparticles varied with respect to time (30 or 120 minutes) and temperature (4° C., 24° C., or 37° C.). In these experiments, $1\times10^8$ colony forming units (CFUs) of *Salmonella* strain BRD509 were incubated with magnetic nanoparticles in saline buffer. At the end of the incubation period, the bacterial suspension was spun down and the supernatant was aspirated. After resuspending the bacterial pellet in 1 ml saline, the bacterial suspension was subjected to a 0.45 Tesla permanent magnet for 15 minutes on the outside surface of the eppendorf tube. The remaining supernatant, presumably containing bacteria without magnetic nanoparticles, was aspirated, and replaced with fresh saline. This procedure was repeated three times. Aliquots were removed from the bacterial suspension before and after each wash cycle and plated to determine the actual count of bacterial CFUs.

Using this procedure, the number of bacterial CFUs remaining after four cycles of magnetic separation and washing (which most likely represents the number of bacteria actually associated with magnetic nanoparticles) was determined, and hence the percentage of bacteria associated with the magnetic nanoparticles was calculated. The results of this analysis showed the reduction in the number of *Salmonella* organisms without magnetic nanoparticles following co-incubation with magnetic nanoparticles at 24° C. for 120 minutes after each cycle of wash. This demonstrates that all bacteria not associated with nanoparticles are effectively removed by the third wash cycle. Furthermore, as shown in the data in Table 3, varying the incubation conditions have a clear impact on the uptake of magnetic nanoparticles by the bacteria. Incubation of magnetic nanoparticles with live *Salmonella* organisms at room temperature resulted in uptake of about six percent ($6\times10^6$), which was sufficient for the loading purpose. The fact that the association appears to be strong suggests that it is feasible to use the *Salmonella* organisms loaded with magnetic nanoparticles in tumor-targeting in vivo.

TABLE 3

Relative efficiency of magnetic nanoparticle uptake by *Salmonella* under different incubation conditions

| Incubation Conditions | | Percent of MNP |
|---|---|---|
| Time (minutes) | Temperature (° C.) | loaded with bacteria |
| 30 | 37 | 3.8% |
| 120 | 37 | 4.0% |
| 30 | 24 | 4.3% |
| 120 | 24 | 6.0% |
| 30 | 4 | 1.0% |
| 120 | 4 | 5.0% |

To show the preferential tropism of bacteria to tumor sites, a study was performed where mice previously implanted with B16F1 melanoma were treated with a single i.p. injection of either BRD509 or GIDIL2 strain of *S. typhimurium*. On day seven post treatment, mice were sacrificed and tissue homogenates were prepared from tumor, liver, and mesenteric lymph nodes (MLN).

The toxicity of the magnetic nanoparticles was investigated, and the experiments determined that the cell morphology did not change. In particular, magnetic nanoparticles were incubated with fibroblasts and Caco-2 cells lines for 24 hours to test their potential toxic effect on normal human and cancer human cells. Three different concentrations of magnetic nanoparticles were used in the experiment, and the cells were examined using light microscopy. Cell morphology of the normal human and cancer human cells remained unchanged during the entire incubation period. There was no toxic response observed for the bacteria incubated with magnetic nanoparticles.

During use, a patient, which may be a human or an animal, may be treated with hyperthermia treatment or inflammation mediated temperature variation at a target tissue. The hyperthermia treatment may be any known or yet to invented hyperthermia treatment. The monitoring agents may be placed, through injection of a mixed solution of the monitoring agents or otherwise, into a bloodstream of a patient. The monitoring agents may then be subjected to an alternating magnetic force to heat the monitoring agents. The monitoring agents and the surrounding target tissue may be scanned to create an image. The image may be analyzed to determine the temperature of the monitoring agents and to determine whether the surrounding target tissue has the same temperature as the monitoring agents.

In other embodiments, a predetermined concentration of bacteria loaded with monitoring agents may be placed into a bloodstream feeding a tumor to identify the temperatures of the tumors within the patient. Once in the bloodstream, the bacteria seek the tumors. Once the bacteria locates the tumors, the bacteria enters the tumors and resides therein. If no tumor is present, the attenuated bacteria strains are passed out of the patient within 24 hours of being injected into the patient. The above process may be repeated to determine the temperature of the tumor.

Figure 2:
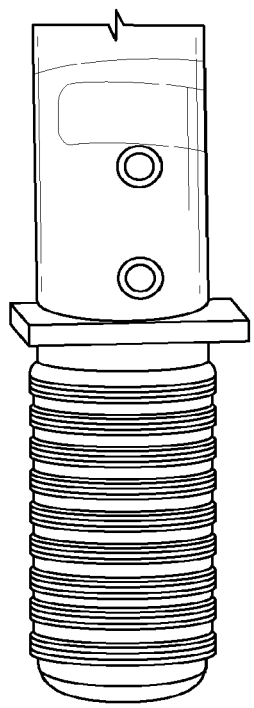
FIG. 2 is a perspective view of an alternating magnetic field generator.
Figure 3:
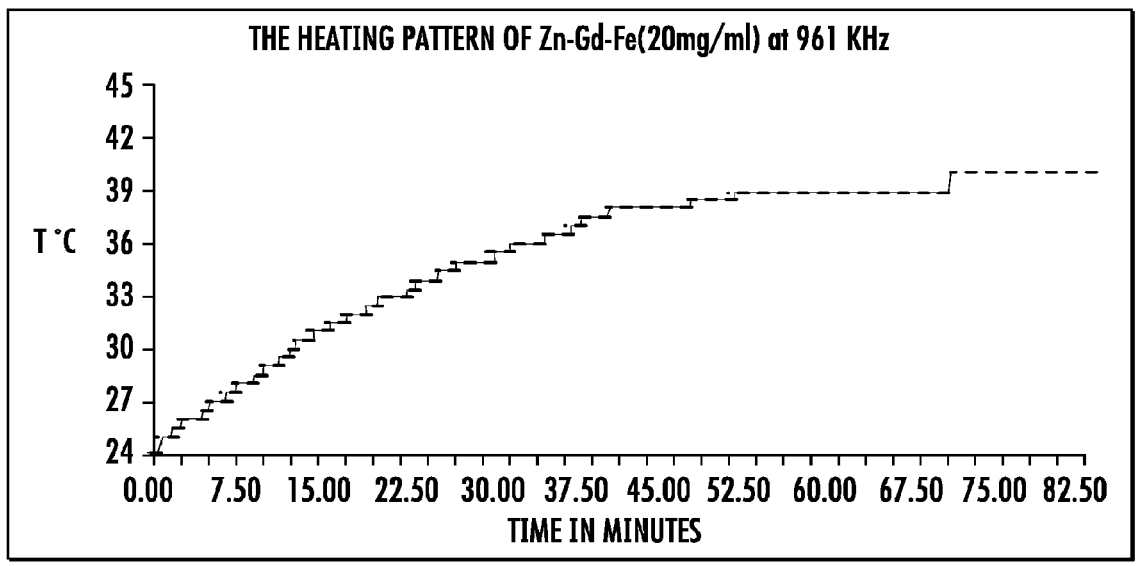
FIG. 3 is a diagram illustrating the self-controlled temperature rise when the hyperthermia agent is placed in an alternating magnetic field.
Figure 4:
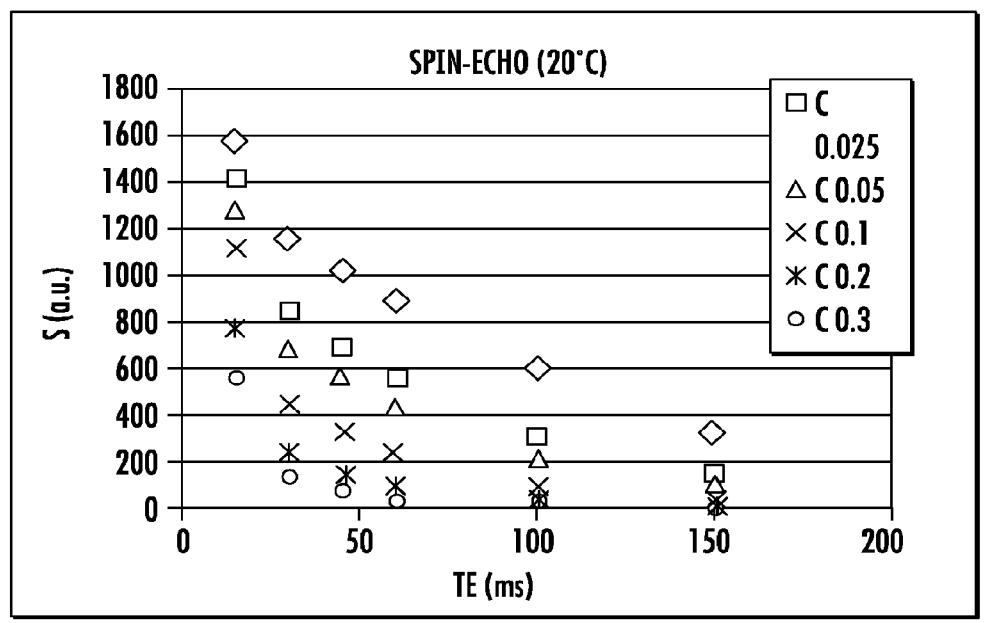
FIG. 4 is a graph of Spin-echo signal versus echo-time for 20 degrees celsius.
Figure 5:
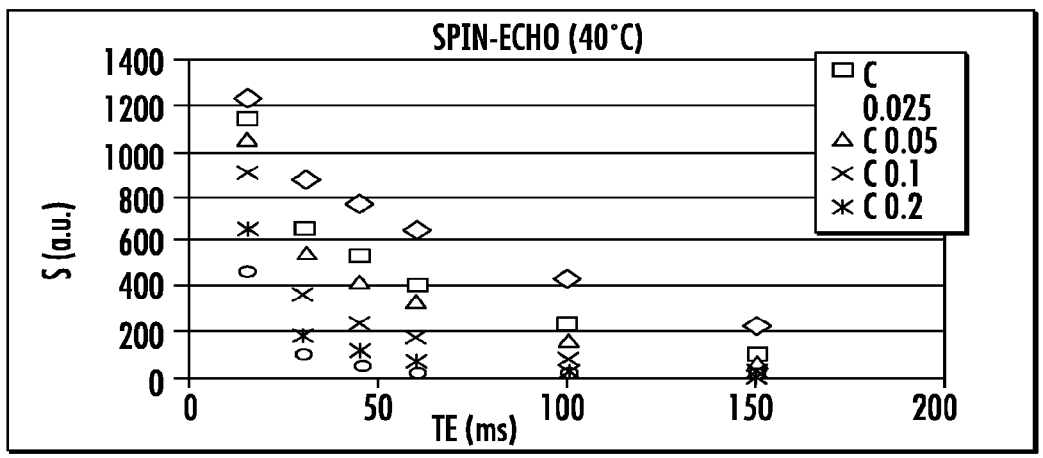
FIG. 5 is a graph of Spin-echo signal versus echo-time for 40 degrees celsius.
Figure 6:
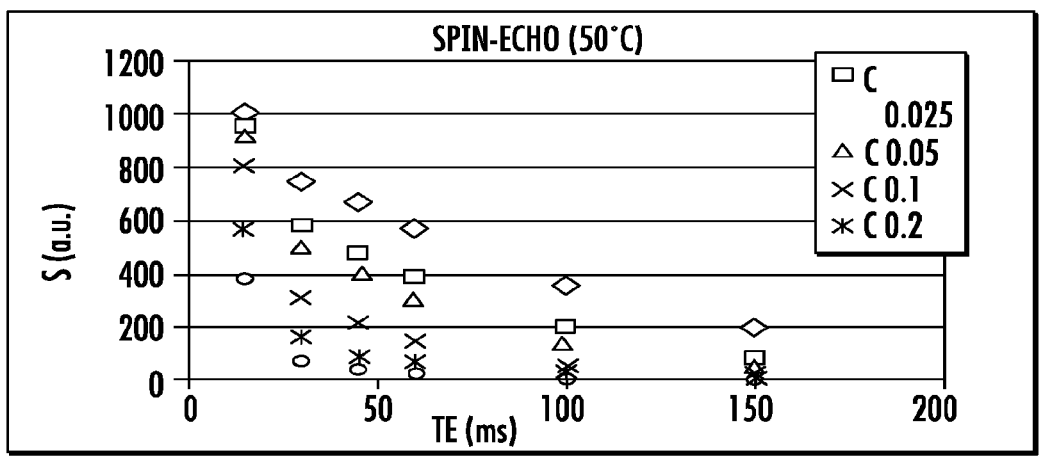
FIG. 6 is a graph of Spin-echo signal versus echo-time for 50 degrees celsius.
Figure 7:
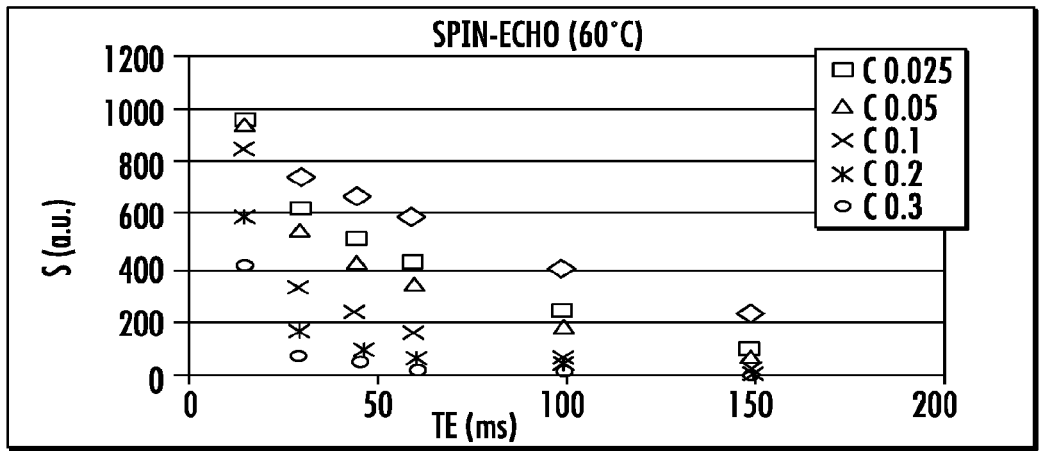
FIG. 7 is a graph of Spin-echo signal versus echo-time for 60 degrees celsius.
Figure 8:
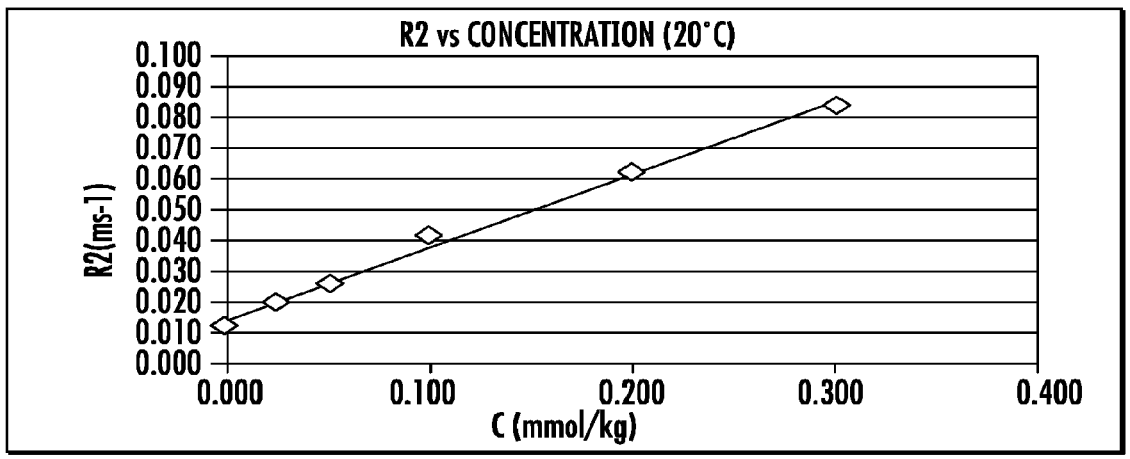
FIG. 8 is a graph of R2 versus concentration of MnGdFe nanoparticles for 20 degrees Celsius.
Figure 9:
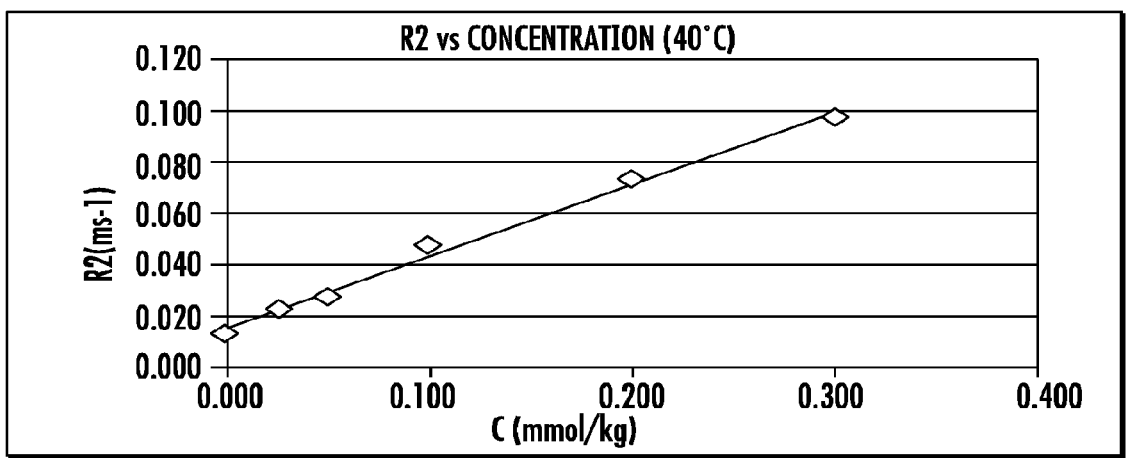
FIG. 9 is a graph of R2 versus concentration of MnGdFe nanoparticles for 40 degrees Celsius.
Figure 10:
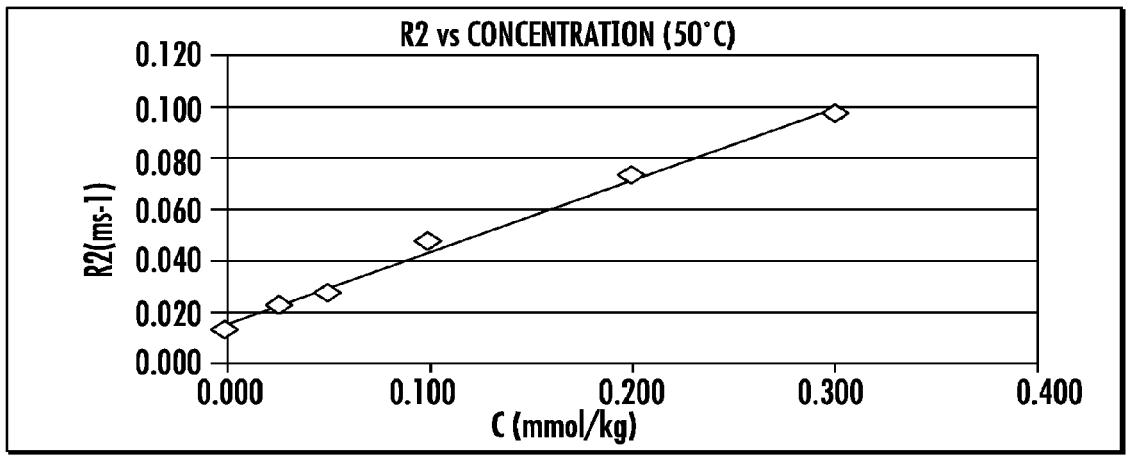
FIG. 10 is a graph of R2 versus concentration of MnGdFe nanoparticles for 50 degrees Celsius.
Figure 11:
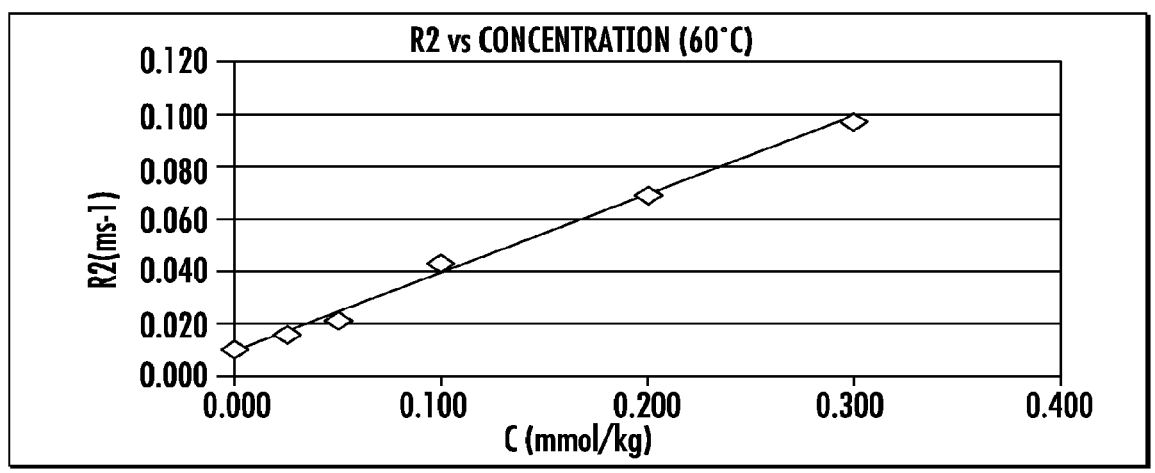
FIG. 11 is a graph of R2 versus concentration of MnGdFe nanoparticles for 60 degrees Celsius.

An alternating magnetic field may then be applied using a generator, such as the generator shown in FIG. 2, in proximity of the tumor location 24 hours after administering the loaded bacteria to the patient. The magnetic nanoparticles induce heating within the tumor tissue. In embodiments where the monitoring agents are those having a Curie temperature less than a critical temperature of tissue at which the tissue is compromised, the magnetic nanoparticles when subjected to the alternating magnetic field heat up to a predetermined Curie temperature and do not increase in temperature beyond the Curie temperature, as shown in FIG. 3. After the magnetic nanoparticles have been heated, a scan may be taken to determine the temperature of the magnetic nanoparticles and compare the nanoparticles to the surrounding tissue to determine the temperature of the surrounding tissue.

The foregoing is provided for purposes of illustrating, explaining, and describing embodiments of this invention. Modifications and adaptations to these embodiments will be apparent to those skilled in the art and may be made without departing from the scope or spirit of this invention.

I claim:

1. A method of monitoring temperature of tissue, comprising:
   administering at least one magnetic nanoparticle to a patient, wherein the at least one magnetic nanoparticle has a known magnetic moment profile that correlates with particular temperatures and wherein the at least one magnetic nanoparticle has been attached to an outer surface of an attenuated bacteria strain via incubating the attenuated bacteria strain with the at least on magnetic nanoparticle;
   subjecting the patient to a magnetic field;
   scanning the patient at a target site thereby creating a scanned image to identify A magnetic moment of the at least one magnetic nanoparticle;
   identifying the temperature of the at least one magnetic nanoparticle;
   comparing the at least one magnetic nanoparticle with surrounding tissue on the scanned image; and
   determining a temperature of the surrounding tissue.

2. The method of claim 1, wherein administering the at least one magnetic nanoparticle to a patient comprises administering the at least one magnetic nanoparticle to a patient, wherein the at least one magnetic nanoparticle further comprises a biocompatible, thermosensitive coating encapsulating the at least one magnetic nanoparticle.

3. The method of claim 1, wherein administering the at least one magnetic nanoparticle to a patient comprises administering the at least one magnetic nanoparticle to a patient, wherein the at least one magnetic nanoparticle is selected from the group consisting of MnGdFe and ZnGdFeO.

4. The method of claim 1, wherein administering the at least one magnetic nanoparticle to a patient comprises administering the at least one magnetic nanoparticle to a patient, wherein the at least one magnetic nanoparticle comprises a combination of magnetic and nonmagnetic materials.

5. The method of claim 1, wherein administering the at least one magnetic nanoparticle to a patient comprises administering the at least one magnetic nanoparticle to a patient, wherein the at least one magnetic nanoparticle has a cross-sectional width of between five nm and one micron.

* * * * *